United States Patent [19]
Dix

[11] Patent Number: 5,454,386
[45] Date of Patent: Oct. 3, 1995

[54] DENTAL FLOSS DEVICE

[76] Inventor: Sean Dix, 145 E. 15th St., Apt. #12A, New York, N.Y. 10003

[21] Appl. No.: 251,046

[22] Filed: May 31, 1994

[51] Int. Cl.⁶ .................................................. A61C 15/00
[52] U.S. Cl. .................................................. 132/323
[58] Field of Search ................... 132/323, 324, 132/325, 326, 327; 242/580, 584.1

[56] References Cited

U.S. PATENT DOCUMENTS

| | | | |
|---|---|---|---|
| 664,014 | 12/1900 | Coryell | 132/323 |
| 1,559,320 | 10/1925 | Hirsch. | |
| 2,162,240 | 6/1939 | Boldusoff | 132/327 |
| 2,866,436 | 12/1958 | Swain et al. | 242/580 X |
| 3,246,729 | 4/1966 | Bishop | 242/584.1 X |
| 4,006,750 | 2/1977 | Chodorow. | |
| 4,016,892 | 4/1977 | Chodorow. | |
| 4,034,770 | 7/1977 | Trecker. | |
| 4,050,470 | 9/1977 | Miller. | |
| 4,162,687 | 7/1979 | Lorch | 132/323 |
| 4,403,625 | 9/1983 | Sanders. | |
| 4,638,824 | 1/1987 | De La Hoz. | |
| 4,729,392 | 3/1988 | Tenny | 132/323 |
| 4,807,651 | 2/1989 | Naydich. | |
| 4,807,752 | 2/1989 | Chodorow. | |
| 4,926,820 | 5/1990 | Wearn | 132/323 |
| 5,222,510 | 6/1993 | Zuehlsdorf. | |
| 5,224,501 | 7/1993 | McKenzie. | |

Primary Examiner—Nicholas D. Lucchesi

[57] ABSTRACT

A dental floss device includes two ring portions having a tongue for holding a segment of dental floss with a closed loop at either end. The tongue opens into the open center of the ring, the tongue being defined by at least one groove opening into the open center of the ring and running to an end portion located towards an outside face of the ring. The groove also opens along its entire length to a top face of the ring at two spaced apart locations.

21 Claims, 2 Drawing Sheets

DENTAL FLOSS DEVICE

The present invention relates to a dental floss device. More particularly, the present invention relates to a device comprising two ring elements each having a tongue adapted to receive and retain a segment of dental floss having closed loops at either end which device can be easily manipulated within the mouth for improved flossing.

BACKGROUND OF THE INVENTION

Standard dental floss consists of a thin string or ribbon, usually of plastic or the like, which is stored within a container. Typically, the container acts as a dispensing device, and has a cutting element thereon for cutting a piece of dispensed floss at a desired length. This simple segment of floss is then wound at both ends about a finger on each hand, and held in place by an adjacent finger. Accordingly, when dental floss is used in this manner, it requires that two fingers on each hand be placed within the mouth to achieve the desired flossing action. Furthermore, when any type of turning or rotational motion is required to reach the back teeth, the problem of having four fingers inside the mouth becomes amplified.

The advantage of providing a dental floss device utilizing finger loops was taught by Trecker in U.S. Pat. No. 4,034,770. The use of finger loops having a segment of dental floss suspended therebetween allows for easier manipulation within the mouth, as only one finger on each is needed, and the floss is securely retained by the fingers without slippage. The Trecker device utilizes the standard floss roll container as described above, except that the floss is tied into finger loops as set intervals. The floss is pulled from the container and cut at a length so as to provide two finger loops formed from floss, with a segment of floss suspended therebetween. While this device is an improvement over the standard flossing device, it suffers from the disadvantage that the finger loops formed of tied-off floss ribbon will have the tendency to cause discomfort to the finger when tension is applied during flossing operation. In addition, it is likely that the roll of floss having the tied-off loops thereon would tend to become tangled within the container, thereby resulting in inoperativeness of the device.

Some of the disadvantages of the Trecker device are addressed in U.S. Pat. No. 4,638,824 to De La Hoz, which teaches two rigid finger rings adapted to removably retain a standard segment of dental floss therebetween. The finger rings have a retaining portion extending laterally from the ring portion, the retaining portion having three cut out prongs extending slightly upwardly, which alternate with respect to the direction in which they open. The end portion of a cut segment of floss is then wound around the three prongs to retain the floss. The De La Hoz device suffers from a disadvantage in that the standard floss segment will have a tendency to either pull out of the retaining prongs or to be cut at the point of retention as a result of the strong force exerted during flossing operation. In addition, the fact that the retaining prongs extend upwardly from the flat surface of the retaining portion leaves open the possibility that the prongs could cause injury to the inside of the mouth. Furthermore, the manipulation of the end of the floss segment to wind it around the three prongs may be difficult for those persons lacking the requisite dexterity.

It is therefore an object of the present invention to provide a dental floss device which requires a minimal degree of finger protrusion into the mouth, but which provides the necessary leverage to achieve proper flossing action, and which furthermore allows for easy rotation of the fingers within the mouth to reach the back teeth.

It is a further object of the present invention to provide a dental floss device which avoids economic and environmental waste by providing a reusable floss retaining portion which is used in conjunction with a floss portion replaced after each use.

It is a still further object of the present invention to provide a dental floss device having finger rings which are comfortably worn on the fingers, and which do not have upwardly extending protrusions which may cause injury to the mouth.

It is another object of the present invention to provide retaining means on the finger rings which act in conjunction with specially adapted floss segments for simple, secure, one-step engagement between the floss segment and the finger rings.

SUMMARY OF THE INVENTION

Accordingly, the present invention provides for a dental floss device comprising two ring portions and a floss portion held therebetween, whereby the ring portions are placed on a finger of each hand of a user, resulting in an improved flossing mechanism which requires that only two fingers be placed within the mouth. Additionally, the device of the invention provides for increased leverage and mobility within the mouth, resulting in ease of flossing and improved results.

The ring portions should be sized to fit over and be retained upon a finger of the user, and the floss portion should be of a size which will allow for full extension between two fingers within the mouth, generally less than about four inches. The ring portions and floss portions may form a unified device which will be wholly discarded after each use. Preferably, the ring portions are specially adapted to receive and removingly retain a segment of floss, which segment of floss can be removed from the rings and discarded, whilst the ring portions are fitted with a new segment of floss and reused. The ring portions are adapted to receive a specially formed floss portion, which floss portion has closed loops at either end which engage with a mating receiving means in the form of a tongue on each ring portion. Again, the specially formed floss portion can be removed from the ring portions and discarded after each use, while the ring portions may be used repeatedly.

BRIEF DESCRIPTION OF THE DRAWINGS

The invention will now be described with respect to the following drawings.

DETAILED DESCRIPTION OF THE INVENTION

Figure 1:
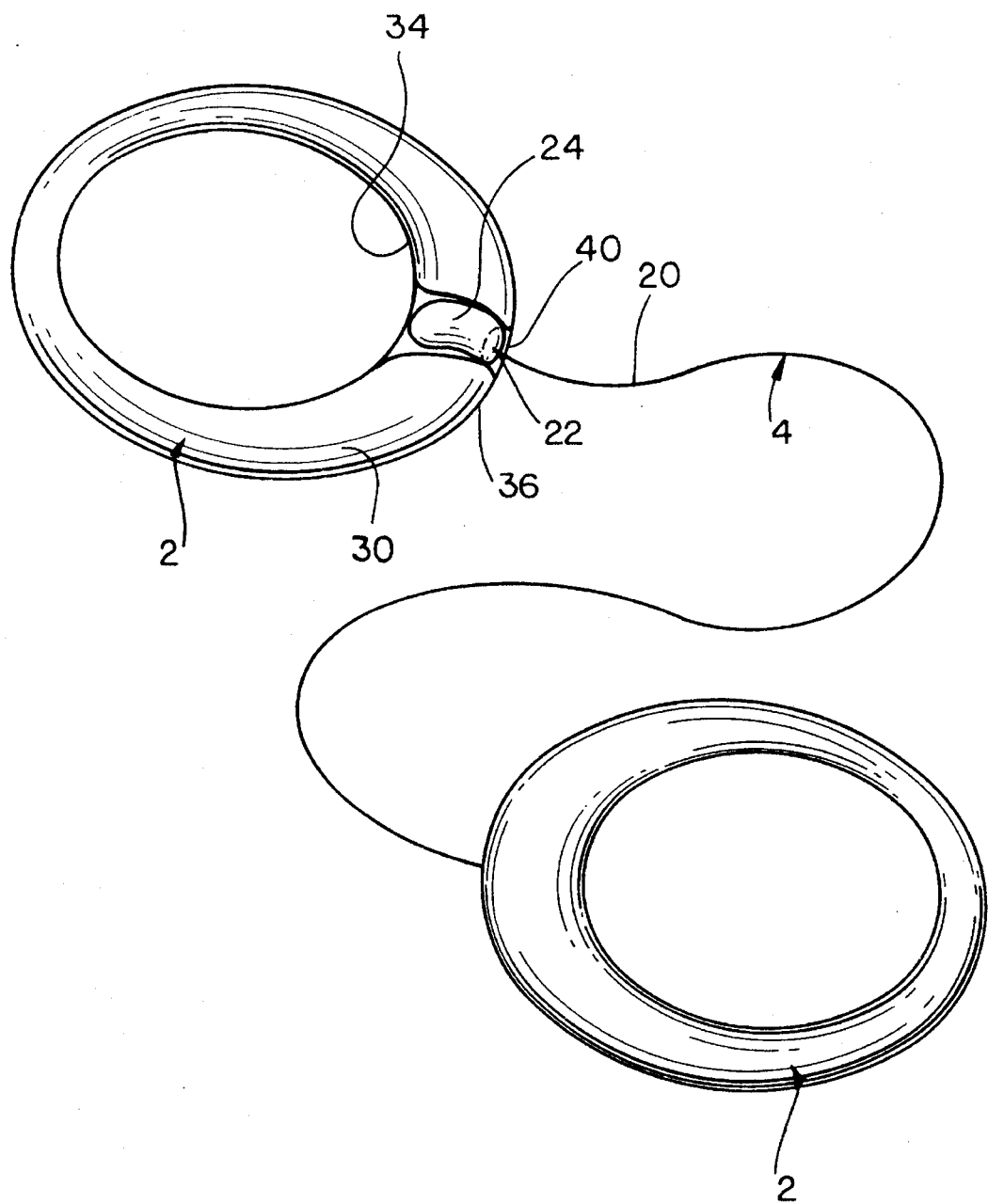
FIG. 1 is a perspective view showing the dental floss device of the invention in a one groove embodiment, with one ring shown in top perspective while the other ring is shown in bottom perspective.
Figure 2:
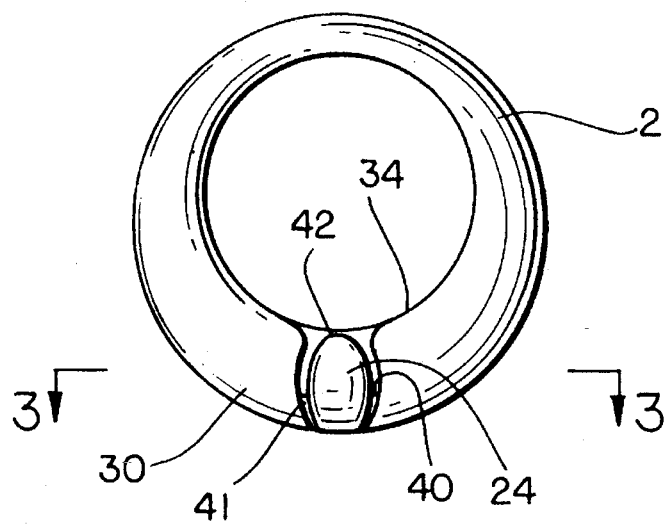
FIG. 2 is a top plan view of a ring portion of the device in a one groove embodiment.

As shown in FIG. 1, the invention comprises two separate ring portions 2 and a floss portion 4 held therebetween. The ring portions 2, which may be toroidal or flat, are generally sized to fit around the finger of a human user. Ring portions of varying inside diameters may be provided to allow the user to choose the appropriate size. In addition, the ring portions may be made of resilient material to allow for different finger sizes, and also to provide added comfort to the fingers during flossing activity by relieving excess pressure upon the fingers. Furthermore, the inside diameter of the ring portions should be relatively smooth and free of protuberances, so as to protect and provide comfort for the finger. The floss portion 4 comprises a standard segment of dental floss, usually a plastic ribbon for insertion between adjacent teeth. During use, one ring portion 2 is placed securely about and retained upon a finger on each hand. The user then manipulates the segment of floss within the mouth by simply moving the two engaged fingers.

The floss portion 4 comprises a segment of floss 20 having at either end closed loops 22 which are engageable with a tongue 24 on each ring portion 2. The tongues 24 are formed to receive and retain the loops 22 to thereby hold the floss portion 4 securely between the two ring portions 2.

Figure 4:
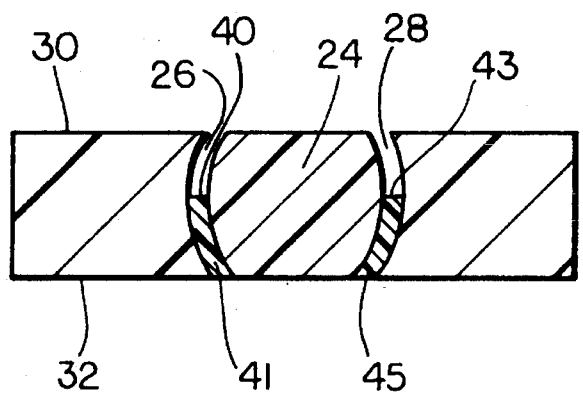
FIG. 4 is a cross-sectional view of a two groove embodiment taken along line III—III.

The tongue 24 is formed integral with the ring portion and extends generally towards the center of the ring so as to retain a floss loop 22 held thereon when force is applied to the loop in the direction away from the ring center. Preferably, the tongue 24 is situated entirely within the generally smooth continuous boundaries of the ring portion, so as to avoid unnecessary protrusions which could irritate the finger or mouth. The tongue 24 may be formed, as in FIG. 4, by two generally lateral grooves 26, 28, opening to the top 30 and bottom faces 32 of the ring 2, open to the inside face 34 of the ring 2 and running to an end abutment portion 40 located towards the outside face 36 of the ring 2 but terminating within the ring.

In a preferred embodiment, the face 41 of the end portion may be slanted so that a top region 43 of the groove opens farther towards the outside face 36 of the ring than does the lower region 45 of the groove. The lower region 45 of the groove meets the end face 41 at a point closer towards the inside of the ring to provide stability to the tongue. This arrangement further allows for maximum leverage upon the floss portion, which will emerge from the ring towards the outside face 36.

The grooves may advantageously approach each other, as shown in FIG. 1, as they reach the end portion 40, so as to better retain the loop 22 therein. In another advantageous embodiment, the width of the grooves themselves may narrow as they approach the end portion, so that the floss string of which the loop 22 is composed will be squeezed and retained within the end of the groove upon insertion. Furthermore, for ease of application of the loop onto the tongue 24, the tongue may be tapered at its free end 42.

Figure 3:
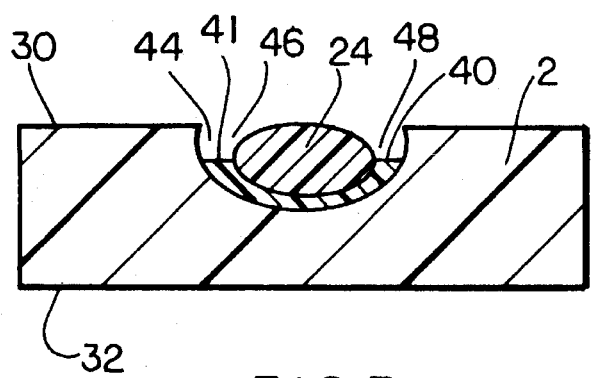
FIG. 3 is a cross-sectional view taken along line III—III.

FIG. 3 shows an alternative formation of the tongue, in which a single groove 44 opens at two spaced apart locations 46, 48 to the top face 30 of the ring 2. The single groove 44 runs cross-wise from one top opening 46 to the other 48 through the ring portion. Otherwise, the single groove 44 is formed in similar fashion to the two groove 46, 48 embodiment discussed above, terminating in a single end portion 40.

The dimensions of the tongue 24 and loop 22 should be coordinated such that the loop can be fitted over the tongue and pulled through the grooves upon application. In addition, the loop should be sized to be slightly larger than the circumference of the widest portion of the tongue, so that once fitted around the tongue and pulled to the end portion, the loop will remain taught and fixed in the groove during flossing activity.

To use the device during a flossing operation, a floss segment 4 having two looped ends 22 is fitted to two rings 2, each loop 22 being fitted around the tongue 24 of one of the rings and pulled along the length of the tongue 24 away from the center of the ring, through the groove 44, until the loop 22 is retained at the end portion 40 of the groove 44, at the point where the tongue 24 is attached to the ring 2. The floss segment 4 thus extends from the attached loop 22 to the outside of the ring. During flossing activity, force is applied by the fingers within the rings in a direction from the tongue towards the center of the ring. Simultaneously, the floss loop is being pulled in the opposite direction by the finger of the other hand. During this operation, the loop is retained against the end point, which end point faces the center of the ring and applies an opposing force against the loop in this same direction. When flossing is completed, the loop may be pulled via the floss segment towards the center of the ring, along the tongue, and removed from the open end of the tongue. At this point, a new floss segment may be applied to the rings.

It is contemplated that the invention encompasses a dental floss device comprising two ring portions and a floss portion held therebetween as described above. In addition, the invention comprises a dental floss device kit, in which two separate ring portions and at least one (and preferably a plurality of) separate floss portion are provided for easy construction of the dental floss device by the user. Furthermore, the invention resides in a ring portion for holding dental floss as described above.

What is claimed is:

1. A dental floss device comprising two finger sized ring portions and a floss portion held therebetween, each ring portion having a tongue which receives and retains thereon an end of the floss portion, the floss portion comprising a segment of floss and a closed loop at each end thereof for engagement with the tongue, wherein the tongue of each ring is defined by a at least one groove opening into the open center of the ring and running to an end portion located towards an outside face of the ring, the at least one groove also opening along its entire length to a top face of the ring at two spaced apart locations.

2. The device of claim 1 wherein said at least one groove comprises a single groove running cross-wise through the body of the ring from one top face opening to the other.

3. The device of claim 1 wherein each tongue is tapered at its free end.

4. The device of claim 1 wherein the two top face openings of the at least one groove approach each other as they reach the end portion.

5. The device of claim 1, wherein the at least one groove comprises opposing walls, wherein the width of the at least one groove gradually narrows as it approaches the end portion so as to engagingly retain one of said floss loops between said two opposing walls at said end portion.

6. The device of claim 1 wherein the end portion comprises an abutment face slanted upward from a bottom face of the ring toward said top face thereof, and the openings of the at least one groove extends to said outside face of the ring.

7. The device of claim,1 further comprising two spaced apart openings on a bottom face of each said ring along the entire length of said at least one groove each of said bottom face openings corresponding to one of said two spaced apart top face openings, to thereby form two separate grooves, one of said two separate grooves running from a first top face opening to a corresponding first bottom face opening, and the other of said two separate grooves running from a second top face opening to a corresponding bottom face opening.

8. A dental floss kit comprising two separate ring portions and a separate floss portion, wherein each ring portion has a tongue for receiving and retaining thereon an end of the floss portion, the floss portion comprising a segment of floss and a closed loop at each end thereof for engagement with one of said tongues of each ring wherein the tongue is defined by a at least one groove opening into the open center of the ring and running to an end portion located towards an outside face of the ring, the groove also opening along its entire length to a top face of the ring at two spaced apart locations.

9. The kit of claim 8 wherein said at least one groove comprises a single groove running cross-wise through the body of the ring from one top face opening to the other.

10. The kit of claim 8, wherein each tongue is tapered at its free end.

11. The kit of claim 8 wherein the two top face openings of the at least one groove approach each other as they reach the end portion.

12. The kit of claim 8 wherein the at least one groove comprises two opposing walls, wherein the width of the at least one groove gradually narrows as it approaches the end portion so as to engagingly retain one of said floss loops between said two opposing walls at said end portion.

13. The kit of claim 8, wherein the end portion comprises an abutment face slanted upward from a bottom face of the ring toward said top face thereof, and the openings of the at least one groove extends to said outside face of the ring.

14. The kit of claim 8, further comprising two spaced apart openings on a bottom face of each said ring along the entire length of said at least lone groove, each of said bottom face openings corresponding to one of said two spaced apart top face openings, to thereby form two separate grooves, one of said two separate grooves running from a first top face opening to a corresponding first bottom face opening, and the other of said two separate grooves running from a second top face opening to a corresponding bottom face opening.

15. A dental floss holder for holding a segment of dental floss with a closed loop on at least one end thereof, the dental floss holder comprising a ring having a tongue for receiving and retaining the loop, the tongue opening towards the open center of the ring, the tongue being defined by at least one groove opening into the open center of the ring and running to an end portion located towards an outside face of the ring, the at least one groove also opening along its entire length to a top face of the ring at two spaced apart locations.

16. The holder of claim 15, wherein said at least one groove comprises a single groove running cross-wise through the body of the ring from one top face opening to the other.

17. The holder of claim 15 wherein the tongue is tapered at its free end.

18. The holder of claim 15, wherein the two top face openings of the at least one groove approach each other as they reach the end portion.

19. The holder of claim 15, wherein the at least one groove comprises two opposing walls, and wherein the width of the at least one groove gradually narrows as it approaches the end portion so as to engagingly retain a floss loop between said two opposing walls at said end portion.

20. The holder of claim 15, wherein the end portion comprises an abutment face slanted upward from a bottom face of the ring toward said top face thereof, and the openings of the groove means extends to said outside face of the ring.

21. The holder of claim 15, further comprising two spaced apart openings on a bottom face of the ring along the entire length of said at least one groove, each of said bottom face openings corresponding to one of said two spaced apart top face openings, to thereby form two separate grooves, one of said two separate grooves running from a first top face opening to a corresponding first bottom face opening, and the other of said two separate grooves running from a second top face opening to a corresponding bottom face opening.

* * * * *